United States Patent [19]

Fachinetti

[11] 4,423,250

[45] Dec. 27, 1983

[54] PROCESS FOR THE PRODUCTION OF OXYGEN-CONTAINING ORGANIC PRODUCTS

[75] Inventor: Giuseppe Fachinetti, Fauglia, Italy

[73] Assignee: Union Carbide Corporation, Danbury, Conn.

[21] Appl. No.: 273,055

[22] Filed: Jun. 12, 1981

[51] Int. Cl.$^3$ .................. C07C 41/00; C07C 41/12; C07C 43/00

[52] U.S. Cl. .................. 568/678; 568/448; 568/861; 568/902

[58] Field of Search ............... 566/750, 852, 448, 675, 566/674; 560/231, 232; 260/439 R, 601; 518/700, 715; 568/902, 861, 678, 440, 902, 861

[56] References Cited

U.S. PATENT DOCUMENTS

| | | | |
|---|---|---|---|
| 2,636,046 | 4/1953 | Gresham | 560/232 X |
| 3,833,634 | 9/1974 | Pruett et al. | 560/232 X |
| 3,954,883 | 5/1976 | Haag et al. | 560/231 |
| 4,089,881 | 5/1978 | Lukehart | 260/439 R |

OTHER PUBLICATIONS

Tominaga et al., *Tetrahedron Letters*, No. 25, pp. 2217–2220, (1970) "Novel Carbonylation Reaction of Substituted Methinyl Tris(Tricarbonylcobalt) Complexes".

Mueherties et al., *Chemical Reviews*, V79(6), pp. 619–620, (1979).

Geoffroy et al., *Inorg. Chem.* V16(11), (1977).

*Primary Examiner*—Helen M. S. Sneed
*Attorney, Agent, or Firm*—Norman L. Balmer

[57] ABSTRACT

A process for the production of oxygen-containing organic products from the reaction of oxides of carbon and hydrogen in the presence of a cobalt-containing compound of the formula $Co_3(CO)_9C-Y$.

13 Claims, No Drawings

PROCESS FOR THE PRODUCTION OF OXYGEN-CONTAINING ORGANIC PRODUCTS

BACKGROUND OF THE INVENTION

This invention relates to the production of oxygen-containing organic products from the reaction of oxides of carbon and hydrogen in the presence of a cobalt-containing catalyst of the formula $$Co_3(CO)_9C-Y$$

wherein Y is as hereinafter described.

Owing to the limited availability of petroleum sources the cost of producing chemicals from petroleum has been steadily increasing and many have raised the dire prediction of significant oil shortages in the future. Obviously, a different low cost source is needed which can be converted into the valuable chemicals now derived from petroleum sources. Synthesis gas* is one such source which can be effectively utilized in certain circumstances to make chemicals.

*For the purposes of the discussion and descriptions contained herein, mixtures of hydrogen and carbon monoxide, regardless of the amount of each present, will be characterized, for the sake of convenience, as "synthesis gas".

The most desirable aspect of synthesis gas is that it can be produced from non-petroleum sources. Synthesis gas may be derived by the combustion of any carbonaceous material including coal, or any organic material, such as hydrocarbons, carbohydrates and the like. Synthesis gas has for a long time been considered a desirable starting material for the manufacture of a variety of chemicals. A number of chemicals have been made commercially from synthesis gas. Hydrocarbons have been made by the Fischer-Tropsch catalytic reaction. Methanol is commercially manufactured by a heterogeneous catalytic reaction from synthesis gas. Aldehydes and alcohols are made from the reaction of olefins and synthesis gas. If one could expand the production of chemicals in a commercial manner from synthesis gas then one would not be as dependent upon petroleum as the basic raw material even though it is an excellent raw material for making synthesis gas. Accordingly, intense interest in such processes has developed.

Pruett and Walker, U.S. Pat. No. 3,833,634, patented Sept. 3, 1974, describes a process for preparing glycols by reacting an oxide of carbon with hydrogen using a rhodium carbonyl complex catalyst. The examples of the patent compare the reaction of hydrogen and carbon monoxide in the presence of the desired rhodium containing catalyst and other metals. In Example 17 of the patent, the reaction was attempted with dicobalt octacarbonyl as the catalyst using acetic acid as the solvent with a reaction temperature of 230° C., for 2 hours, and "the product contained no polyhydric alcohol," but traces of the mono-and diacetate of ethylene glycol were detected.

Gresham, U.S. Pat. No. 2,535,060, describes a process for preparing monohydric alcohols by introducing carbon monoxide, hydrogen and a hydroxylated solvent into a reaction vessel and heating the mixture in the presence of a ruthenium-containing substance and an alkaline reagent which controls the pH within the range of 7 to 11.5, at a temperature within the range of 150° to 300° C. under a pressure within the range of 200 to 1,000 atmospheres.

U.S. Pat. No. 2,636,046, filed Oct. 16, 1948, to Gresham describes the production of polyfunctional oxygen-containing organic products including such compounds as ethylene glycol, glycerine, and the like.* This is accomplished by the reaction of hydrogen with carbon monoxide in the presence of a solvent to produce glycol. According to this patent, the reaction of carbon monoxide with hydrogen must be at pressures of above 1,000 atmospheres and "particularly above a minimum of about 1,400 atmospheres" in order to obtain the "polyfunctional oxygen-containing organic compounds . . . in excellent yield" (column 2, lines 9-17).

The patent specifically states at column 2, lines 37-43, that:

"[I]n the hydrogenation of oxides of carbon at pressures of 1,000 atmospheres and below, virtually no polyfunctional compounds are produced. At pressures above 1,000 atmospheres and especially at pressures of about 1,500 to 5,000 atmospheres, preferably 2,000 to 5,000 atmospheres, polyfunctional compounds are obtained."

The examples of the U.S. Pat. No. 2,636,046 describe the use of a cobalt catalyst; the patentee, at column 3, line 61, indicates that the catalyst may contain "cobalt, ruthenium, etc."

*Note the evaluation of this work by Rathke and Feder, JACS, 100, pp. 3623-3625 (May 24, 1978).

According to Roy L. Pruett, *Annals, New York Academy of Sciences*, Vol. 295, pages 239-248 (1977), at page 245, metals other than rhodium were tested to determine the production of ethylene glycol from mixtures of carbon monoxide and hydrogen. These metals include cobalt, ruthenium, copper, manganese, iridium and platinum. Of these metals, cobalt was found to have a slight activity, citing British Pat. No. 665,698 which corresponds generally to the last mentioned Gresham U.S. Patent. Pruett stated that such slight activity with cobalt was "qualitatively" in agreement with the results obtained by Ziesecke, 1952, Brennstoff-chem, 33:385.

The production of acetaldehyde from methanol, hydrogen and carbon monoxide in the presence of a cobalt catalyst is disclosed in U.S. Pat. No. 4,151,2098. Similarly, Japanese Publication Nos. JA77/13611 discloses a process catalyzed by cobalt, a halogen, and phosphorus.

The existence of substituted methinyl tris (tricarbonylcobalt) complexes is disclosed in "Novel Carbonylation Reaction of Substituted Methinyl Tris (Tricarbonyl Cobalt) Complexes", K. Tominaga., et al., Tetrahedron Letters, No. 25, 2217-2220 (1970). The complexes disclosed therein are of the general formula $YC-Co_3(CO)_9$ where Y represents hydrogen, alkyl, aryl, halogen, $-COOH$, $-COOR$, $-CH_2CH_2COOH$, $-CH=CHCOOH$, etc. The complexes are employed in a dicarbonylation reaction on the same carbon atom with the metal carbonyl. The reaction employs an organic base and a cobalt-containing catalyst in an alcohol solvent under a carbon monoxide pressure with the exception that methanolysis of $CH_3-C-Co_3(CO)_9$ under hydrogen pressure and hydrogenolysis of $CH_3-C-Co_3(CO)_9$ under a pressure of hydrogen and carbon monoxide are reported. The methanolysis of $CH_3-C-Co_3(CO)_9$ (hydrogen pressure 100 atm) gave 36 percent (basis not reported) methyl propionate, 64 percent 1,1-dimethyoxypropane with a molar ratio of 16:84 respectively. The hydrogenolysis of $CH_3-C-Co_3(CO)_9$ in benzene solution in the presence of hydrogen and carbon monoxide gave a yield of 50 percent (basis not reported) propionaldehyde. It is not clear from the disclosure as to whether an organic baase was employed in the methanolysis and hydrogenolysis reactions.

Recently, the formation of the tricobalt carbonyl anionic cluster [Co$_3$(CO)$_{10}$]$^-$ was reported by G. Fachinetti, J.C.S., Chem. Comm., 396–397 (1979). The molecular structure of LiCo$_3$(CO)$_{10}$—i—Pr$_2$O has been reported by Hans-Norbert Adams, et al., Angew. Chem. Vol. 19, 404–405 (1980).

The preparation and characterization of the acid Co$_3$(CO$_9$C—OH has been reported by G. Fachinetti, J.C.S., Chem. Comm., 397–398 (1978). The crystal and molecular structure of this acid has been discussed by Hans-Norbert Adams, Angew. Chem. Int. Ed., 20, 125–126 (1981). The author, at page 126, suggested the acid Co$_3$(CO)$_9$C—OH as a model for the homogeneous phase hydrogenation of CO to methanol (citing G. L. Geoffroy and R. A. Epstein, Inorg. Chem. 16, 2795 (1977) and E. L. Muetterties, J. Stein, Chem. Rev., 79, 479 (1979) on the hydrogenation of Co$_3$(CO)$_9$C—R to hydrocarbons as additional basis for this suggestion.

The formation of HCo$_3$(CO)$_9$ by the loss of carbon monoxide by the acid Co$_3$(CO)$_9$C—OH has been reported by G. Fachinetti, et al., Angew. Chem., Vol. 18, 619–620 (1979). Further, the latter report shows the formation of Co$_3$(CO)$_9$C—CH$_3$ by the reaction of HCo$_3$(CO)$_9$ and acetylene. The formation and isolation of HCo$_3$(CO)$_9$ is discussed further by G. Fachinetti, Angew. Chem. Int. Ed., 20, 204–206 (1981). In addition, the latter reports the preparations of the triethylamine adduct of Co$_3$(CO)$_9$C—OH and the triethylamine adduct of HCo(CO)$_4$ is reported by F. Calderazzo, J.C.S. Chem. Comm., 183–188 (1981).

SUMMARY OF THE INVENTION

It has been found that oxygen-containing organic products can be produced by the reaction of carbon monoxide and hydrogen in the presence of a novel cobalt-containing compound having the formula:

(Co)$_3$(CO)$_9$C—Y wherein Y is selected to provide the oxygen-containing organic products having at least 2 carbon atoms and 1 oxygen atom more than Y and may be any substituent which will provide for the formation of said products containing at least 2 additional carbon atoms and 1 additional oxygen atom. The substituent Y may be hydrogen, duterium, hydroxyl, alkoxy, alkyl, halogen, —COOH, —COOR, araalkyl, alkylaryl, aryl and the like and preferably is selected from the group consisting of hydrogen, deterium, hydroxyl and alkoxy. The preferred oxygen-containing organic products are those containing 2 carbon atoms and 1 oxygen atom more than contained in the substituent —Y.

DESCRIPTION OF THE INVENTION

The present invention resides in a process for the conversion of mixtures of oxides of carbon and hydrogen to a variety of oxygen-containing organic products by reacting said mixtures in the presence of a cobalt-containing compound having the formula:

(Co)$_3$(CO)$_9$C—Y (hereinafter referred to as the "Cobalt Triad") wherein Y is selected to provide the oxygen-containing organic products having at least 2 carbon atoms and 1 oxygen atom more than Y and may be any substituent which will provide for the formation of said products containing at least 2 additional carbon atoms and 1 additional oxygen atom. The substituent Y may be hydrogen, deuterium, hydroxyl, alkoxy, alkyl, halogen, —COOH, —COOR, araalkyl, alkylaryl, aryl and the like and preferably is selected from the group consisting of hydrogen, deuterium and alkoxy. The preferred oxygen-containing organic products are those containing 2 carbon atoms and 1 oxygen atom more than contained in the substituent Y.

The oxygen-containing organic products formed herein contain at least 2 carbon atoms and 1 oxygen atom more than is present in Y of the Cobalt Triad and preferably contain 2 carbon atoms and 1 oxygen atom more than are present in Y. The typical products include aldehydes, glycol ethers, glycol ether formates, glycol aldehyde, mono- and polyhydric alcohols and the like and mixtures thereof. In particular, when Y is alkoxy the formation of glycol ethers are formed. Other oxygen-containing organic products may be formed depending on the selection of Y.

The mixture of hydrogen and carbon monoxide used herein can be produced from most any material containing carbon and hydrogen. Two types of reactions, for example, can be used for the production of synthesis gas, partial oxidation and steam reforming. Steam reforming is the more important process when natural gas (methane) is the hydrogen-carbon source. Partial oxidation is used primarily for heavy fuel and residue.

The source of the cobalt in the cobalt-containing compound employed in the instant invention can be furnished from a number of sources, for example, any known cobalt source which forms the Cobalt Triad in the reaction mixture under the process conditions; for example, cobalt salts, such as cobalt acetate; cobalt carbonyls such as dicobalt octacarbonyl, methyl cobalt tetracarbonyl, acetyl cobalt tetracarbonyl; cobalt carbonyl anions; and the like.

The preparation of (Co)$_3$(CO)$_9$C—OH by the acidification of [(Co)$_3$(CO)$_{10}$]$^-$ was reported by G. Fachinetti in Chem. Commun., pages 397–398 (1979), said preparation being incorporated by reference herein.

The preparation of the Cobalt Triad wherein Y is other than hydroxyl (—OH), e.g., deuterium, hydrogen, alkoxy and alkyl, may be by any known synthetic preparation as such or the Cobalt Triad may be formed in situ. Exemplary of such preparative techniques are those described: in D Seyferth, J. E. Hallgren, P. L. K. Hung, J. Organometallic Chem. 50, 265, (1973); and R. Markly, I. Wender. R. A. Friedel, F. A. Cotton, H. W. Steanberg, J. Am. Chem. Soc., 80, 6529 (1958); both disclosures being incorporated by reference herein.

The concentration of the Cobalt Triad employed under reaction conditions is not narrowly critical with an effective amount of the Cobalt Triad being employed such that oxygen-containing organic products are formed at a suitable and reasonable reaction rate. The oxygen-containing organic products have 2 carbon atoms and at least 1 oxygen atom more than are present in —Y of the Cobalt Triad, e.g., when —Y is alkoxy (—OR) the predominate reaction product is the glycol ether (HOCH$_2$CH$_2$OR).

Reaction may proceed when employing as little as about 1×10$^{-6}$ weight percent of cobalt (contained in the Cobalt Triad), and even lesser amounts, based on the total weight of reaction mixture. The upper concentration limit can be quite high, e.g., about ten weight percent and higher. Depending on various factors such as the partial pressures of oxides of carbon and hydrogen, the total operative pressure of the system, the operative temperature, other considerations, a concentration of between about $1 \times 10^{-3}$ and about 5.0 weight percent of cobalt (contained in the Cobalt Triad) based on the total weight of reaction mixture, is generally desirable in the practice of the invention.

The reaction between carbon monoxide and hydrogen is effected in a homogenous liquid phase mixture and is carried out at an effective temperature for the reaction, preferably between about 80° C. and about 300° C. and most preferably between about 80° C. and about 140° C., sufficient to produce the oxygen-containing organic products. The process is conducted at an effective pressure which is superatmospheric pressure sufficient to produce the oxygen-containing organic products. Pressures of between about 300 pounds per square inch absolute (psia) and about 15,000 psia, and higher, can be employed. Preferably, pressures in the range of between about 500 psia and about 10,000 psia are employed with between about 500 psia and about 7,000 psia being most preferred.

In practicing the process of this invention, the reaction (or residence) time utilizing the Cobalt Triad, as aforedescribed, can range from about minutes to as long as 10 to 20 hours or more, depending upon the conditions selected; milder conditions providing longer residence times whereas more aggressive, i.e., severe, conditions in terms of pressure and temperature reducing the residence time.

In the practice of the invention a liquid organic solvent is employed to provide a homogeneous liquid phase. Illustrative of the liquid organic solvents which are generally believed suitable in the practice of the invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, tolune, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of oxyethyleneoxypropylene glycol, etc.; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; and others. Nonpolar aromatic solvents such as xylene and benzene are preferred solvents.

In practicing the process of the present invention, the synthesis of the desired oxygen-containing organic products by the reaction of hydrogen with an oxide of carbon in the presence of the Cobalt Triad is suitably conducted under operative conditions, as heretofore described.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. Mixtures of carbon dioxide, carbon monoxide and hydrogen can also be employed. If desired, it is believed that the reaction mixture can comprise steam and carbon monoxide. The "oxide of carbon" as covered by the claims and as used herein is intended to mean carbon monoxide and mixtures of carbon dioxide and carbon monoxide, either introduced as such or formed in the reaction. Preferably, the oxide of carbon is carbon monoxide.

The process of this invention can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotator, oscillation, ultrasonic, etc., are all illustrative of the types of agitation means which are contemplated. Such means are available and well known to the art. The Cobalt Triad may be initally introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of, and the partial pressures exerted by, the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with or without make-up carbon monoxide and hydrogen to the reaction. Recovery of the desired product can be achieved by methods well-known in the art such as by distillation, fractionation, extraction, and the like. A fraction comprising the Cobalt Triad, generally contained in byproducts and/or liquid organic solvent can be recycled to the reaction zone, if desired. All or a portion of such fraction can be removed for recovery of the Cobalt Triad, if necessary, and intermittently added to the recycle stream or directly to the reaction zone.

In carrying out the following examples the Cobalt Triad catalyst was charged to a 50 milliliter stainless steel autoclave with about 15 milliliter of para-xylene, except where noted hereinafter. The Cobalt Triad was employed in an amount of $3.0 \times 10^{-3}$ moles with $1.5 \times 10^{-3}$ moles of dicobalt octacarbonyl being present. Since the Cobalt Triad generates dicobalt octacarbonyl under the process conditions, it is believed that the presence of dicobalt octacarbonyl in the initial reaction mixture is not essential for the production of the reaction products. The autoclave, i.e., reactor, was sealed, purged with argon and then pressurized to the desired reaction pressure, as indicated hereinafter with a gaseous mixture having a 1:1 molar ratio of hydrogen to carbon monoxide. The autoclave and the contents thereof were heated to the reaction temperature as indicated hereinafter, for the specified reaction period during which time the autoclave contents were stirred to obtain through mixing thereof. After the reaction period was complete the contents of the autoclave were analyzed by thin layer chromatography (using silica gel and n-hexane) for the presence of the Cobalt Triad. In each place, the Cobalt Triad catalyst was not observed at the end of the reaction. Instead, analysis of the cooled reaction mixture by infrared spectroscopy indicated the presence of $HCo(CO)_4$ and $Co_2(CO)_8$. The reaction mixture was further analyzed by mass spectroscopy using a Varian (TM) MAT CH7 mass spectometer, 70 eV with an accelerating voltage of 3 Kilovolts and an emission current of 300 milliamperes. The reaction mixture was first analyzed by gas chromatography using a Varian (TM) Aerograph 1400 having a Porapak P (TM) column with a column temperature between about 100° C. and 120° C. The effluent from the gas chromatographic analysis was the reaction mixture sample introduced to the mass spectrometer for analysis. Identification of the oxygen containing organic products was obtained by comparison with standards. The standards were analyzed on a Perkin Elmer (TM) F30 gas chromatograph having a Carbowax W (TM) column.

EXAMPLE 1

$Co_3(CO)_9C-OCH_3$ was prepared, according to the procedure above-cited in D. Seyferth, et al., and employed in the process according to this invention according to the above described experimental procedure. The process was carried out at a pressure of about 115 atmospheres (1690 psia) and at a temperature of about 120° C. for about 15 hours.

A sample was removed from the autoclave after the reaction had proceeded for about 4 hours and analyzed according to the above-described analysis methods. The analysis after 4 hours indicated the presence of glycolaldehyde methyl ether, methanol and dimethyl ether in the molar ratio of about 10:1:1. In addition, a minor amount of 2-methoxyethanol was detected.

After 15 hours the reaction mixture was analyzed by the method described in the Experimental Procedure and the results are reported in Table I.

TABLE I[1,2]

| Product | Conversion (Percent)[3] |
| --- | --- |
| 2-methoxyethanol | 60 |
| dimethylether | 6 |
| 2-methoxyethanol formate | 10 |

[1]The reaction mixture was analyzed immediately after sampling and after treatment with an equal volume of hydrochloric acid. Yields of 2-methoxyethanol and formic acid were determined in the aqueous layer using a Varian Aerograph TM 1400 gas chromatograph having a Porapak PV TM column.
[2]Minor amounts of methanol were detected in the para-xylene solution. The presence of methanol was not analyzed for in the aqueous layer. No analysis was carried out for methane.
[3]Conversion expressed as a mole percent of Cobalt Triad based on moles.

EXAMPLE 2

$Co_3(CO)_9C-H$ was prepared and employed in the process according to this invention using the procedure described in Example 1. The temperature was about 100° C. and the pressure was about 95 atmospheres (1396 psia). The reaction was carried out for about 45 minutes.

The reaction product mixture was analyzed by the method employed in Example 1 with a quantitative yield of acetaldehyde being detected. No analysis for methane was made.

EXAMPLE 3

$Co_3(CO)_9C-D$ (D=deuterium) was substituted for $Co_3(CO)_9C-H$ of Example 2. The reaction product mixture was analyzed as in Example 2 and by mass spectroscopy, as above-described, which indicated a quantitative yield of acetaldehyde with at least about 70 percent by weight of said acetaldehyde comprising duterated aldehyde.

EXAMPLE 4

$Co_3(CO)_9C-(CH_2)_3CH_3$ was prepared according to the above-discussed procedure and employed in the process according to this invention using a procedure described in Example 1. The temperature was about 120° C. and the pressure was about 120 atmospheres. The process was carried out for about 15 hours.

After 3 hours a sample was taken from the reaction mixture and analyzed by gas chromatography as above described. The analysis indicated the presence of hexanaldehyde and 2-methyl pentanaldehyde in a molar ratio of about 3.4.

After 15 hours the reaction product mixture was analyzed by the method employed in Example 1 and the results are reported in Table II.

TABLE II

| Product[1] | Conversion (Percent) |
| --- | --- |
| hexanol | 58 |
| 2-methylpentanol | 17 |
| n-pentane | 5 |
| hexanaldehyde | 1 |
| 2-methylpentanaldehyde | trace |

[1]oxygen-containing organic products
[2]conversion expressed as a mole percent based on moles of Cobalt Triad.

What is claimed is:

1. The process for the production of oxygen-containing organic products which comprises reacting, in a homogeneous liquid phase, carbon monoxide and hydrogen in the presence of an effective amount of a cobalt-containing compound to form said oxygen-containing organic products said cobalt-containing compounds having the formula:

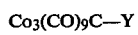

$Co_3(CO)_9C-Y$ wherein Y is selected from the group consisting of hydrogen, deuterium, hydroxy, and alkoxy at an effective temperature and pressure such that the oxygen containing organic product formed contains the substituent Y and at least 2 carbon atoms and 1 oxygen atom more than are present in Y.

2. The process of claim 1 wherein the oxygen-containing organic product has the formula

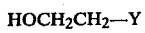

$HOCH_2CH_2-Y$ and the cobalt-containing compound has the formula

wherein Y is hydroxyl or alkoxy.

3. The process of claim 2 wherein Y is alkoxy.

4. The process of claim 1 wherein Y is hydrogen.

5. The process of claim 1 wherein the oxygen-containing organic product contains 2 carbon atoms and 1 oxygen atom more than are present in —Y.

6. The process of claim 1 wherein the temperature is between about 80° C. and about 300° C.

7. The process of claim 6 wherein the temperature is between about 80° C. and about 140° C.

8. The process of claim 1 wherein the pressure is between about 300 psia and about 15,000 psia.

9. The process of claim 8 wherein the pressure is between about 500 psia and about 10,000 psia.

10. The process of claim 1 wherein said homogeneous liquid phase contains a nonpolar solvent.

11. The process of claim 10 wherein the solvent is an aromatic solvent.

12. The process of claim 1 wherein the concentration of the cobalt-containing compound is between about $10^{-6}$ weight percent and about 10 weight percent.

13. The process of claim 12 wherein the concentration of the cobalt-containing compound is between about $10^{-3}$ weight percent and about 5.0 weight percent.

* * * * *